Figure 1:
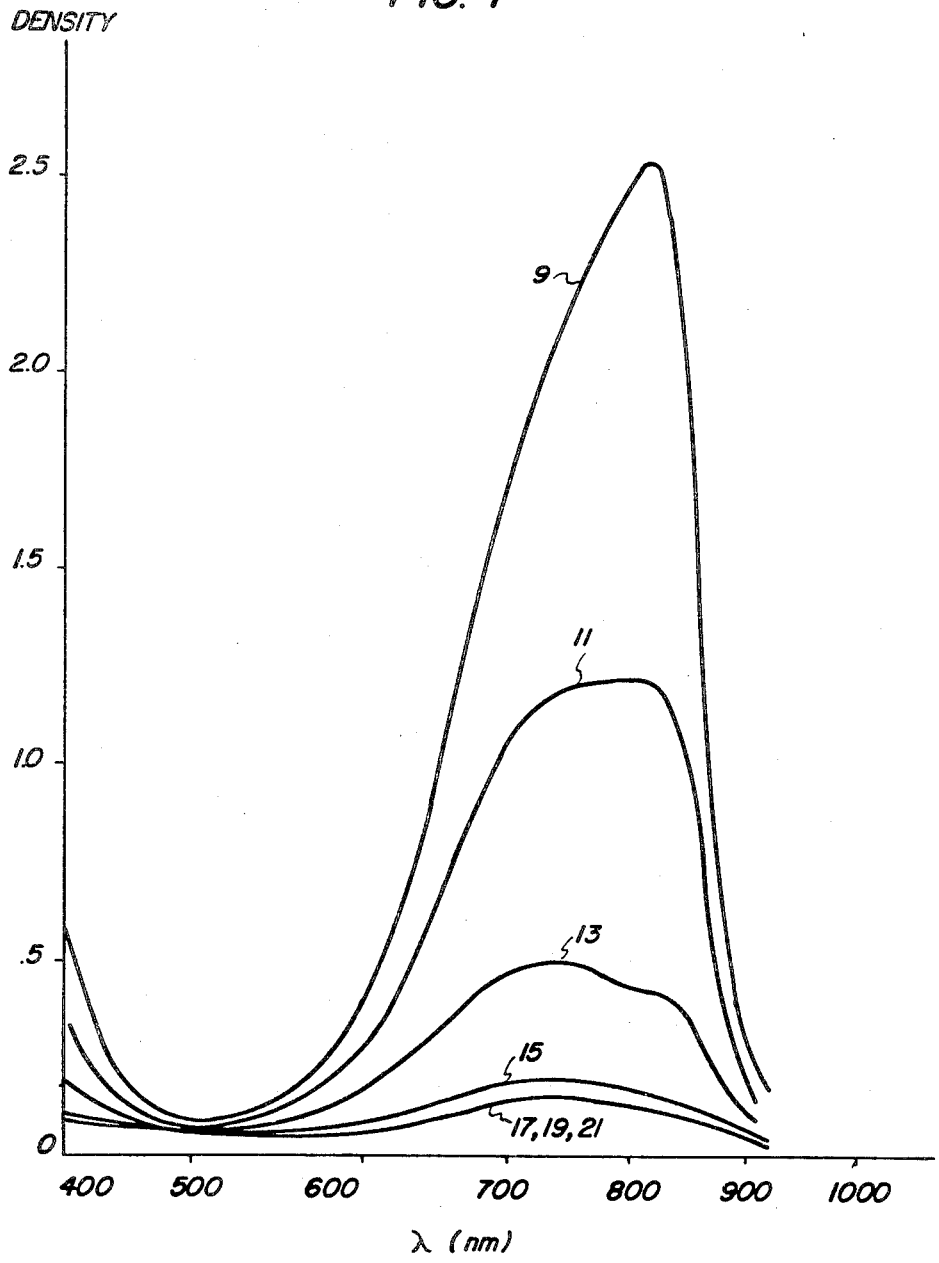
Figure 2:
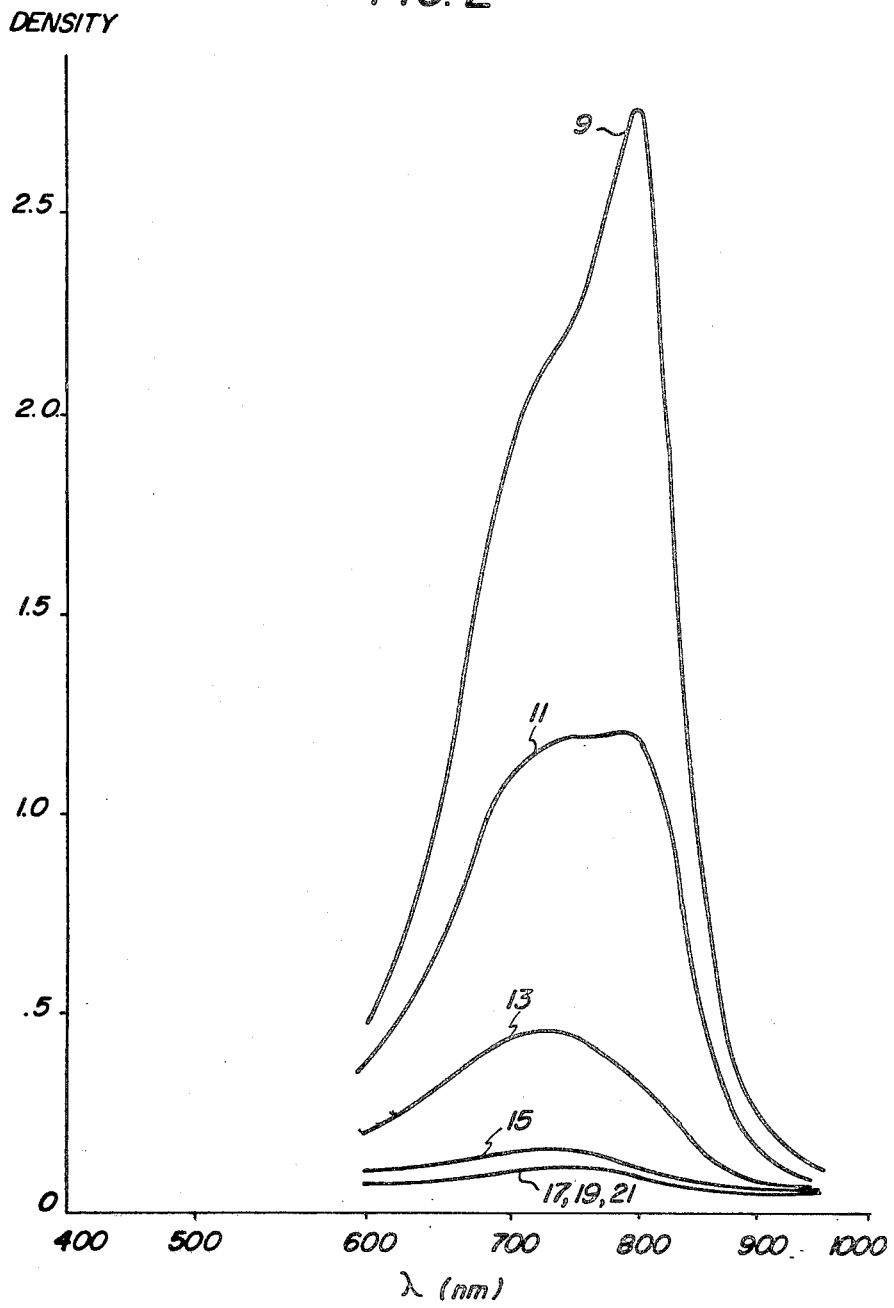
Figure 3:
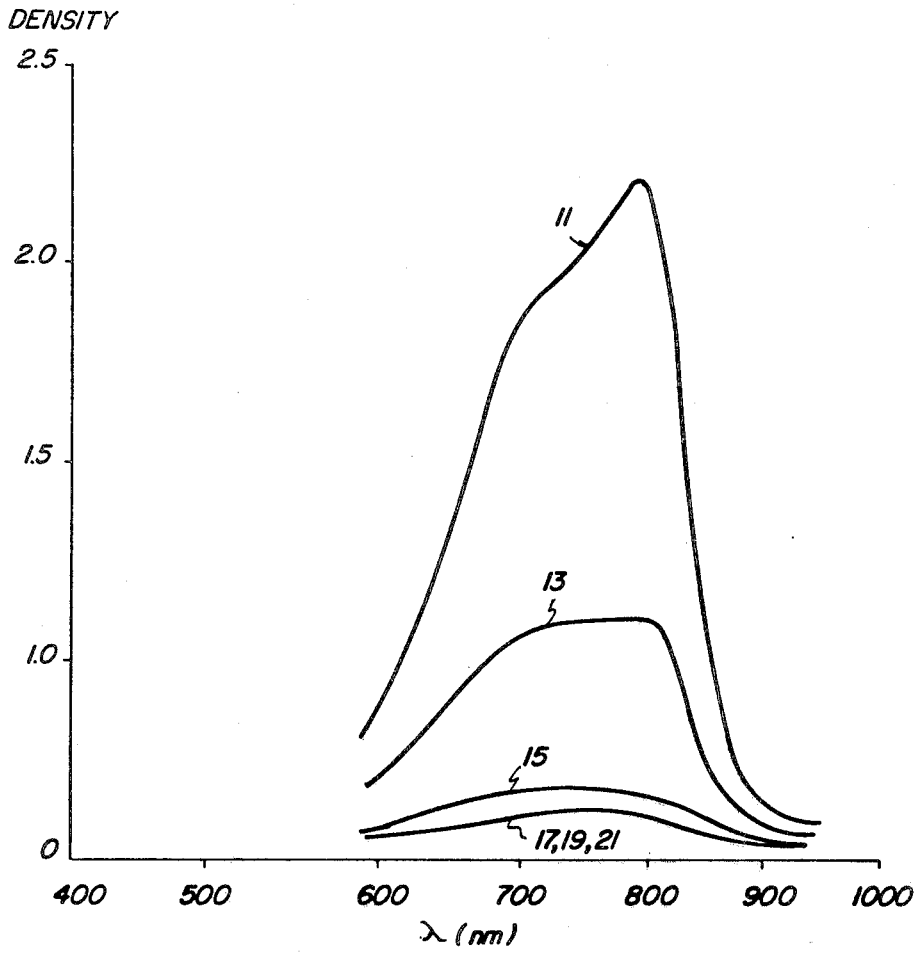
Figure 4:
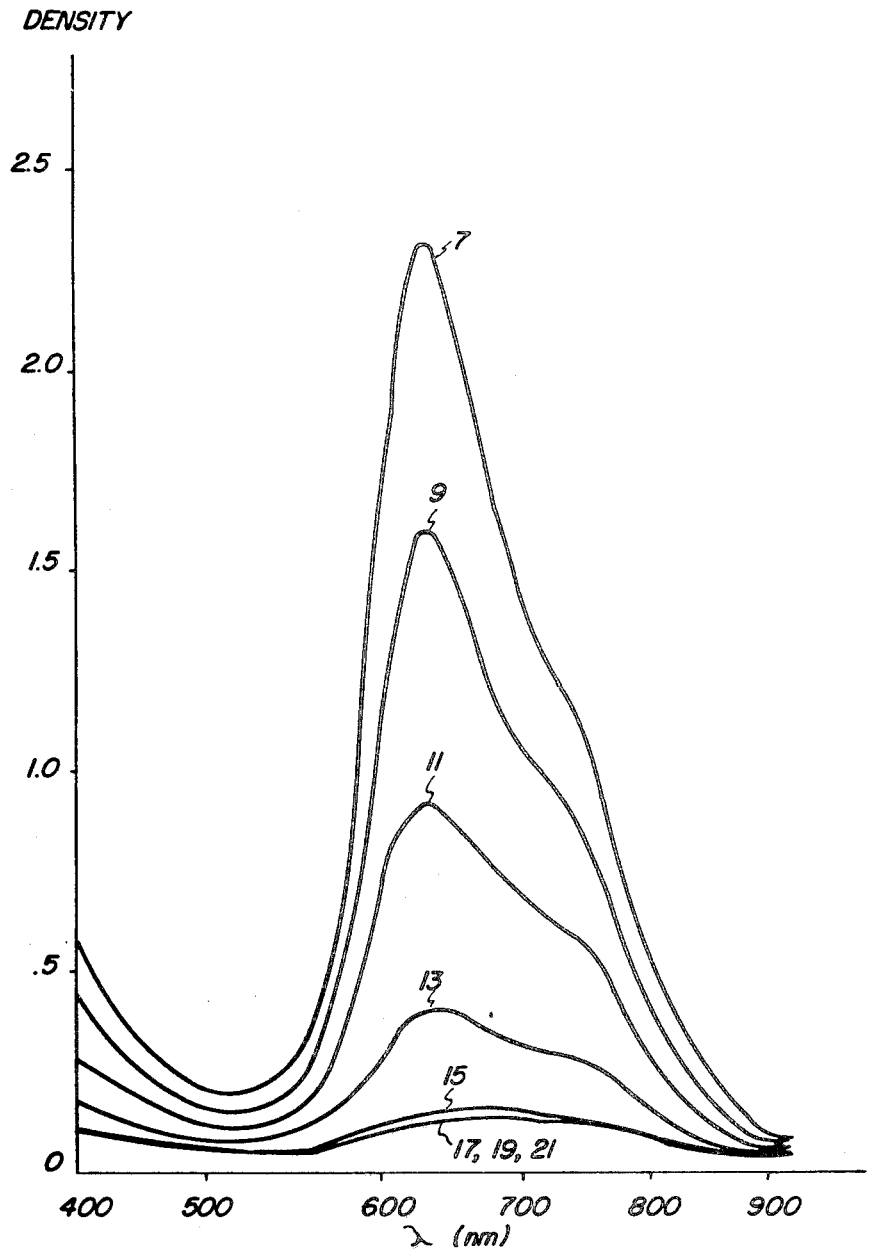
Figure 5:
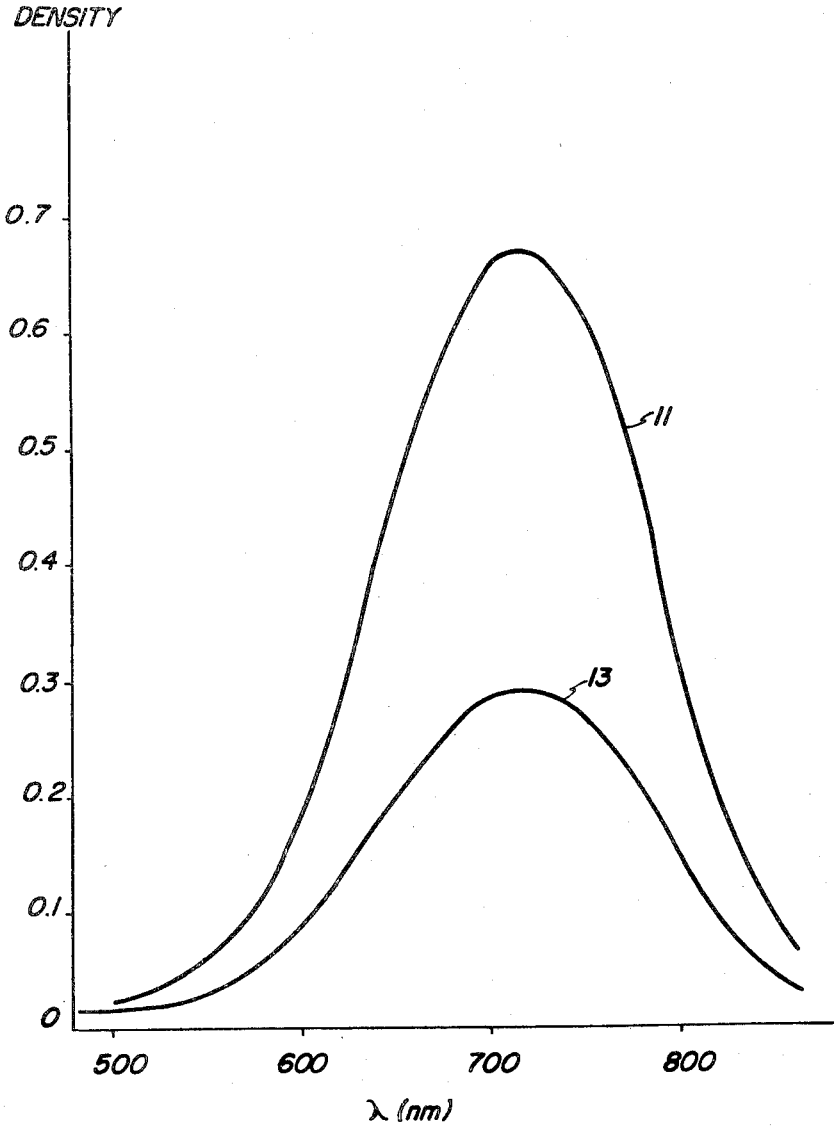
Figure 6:
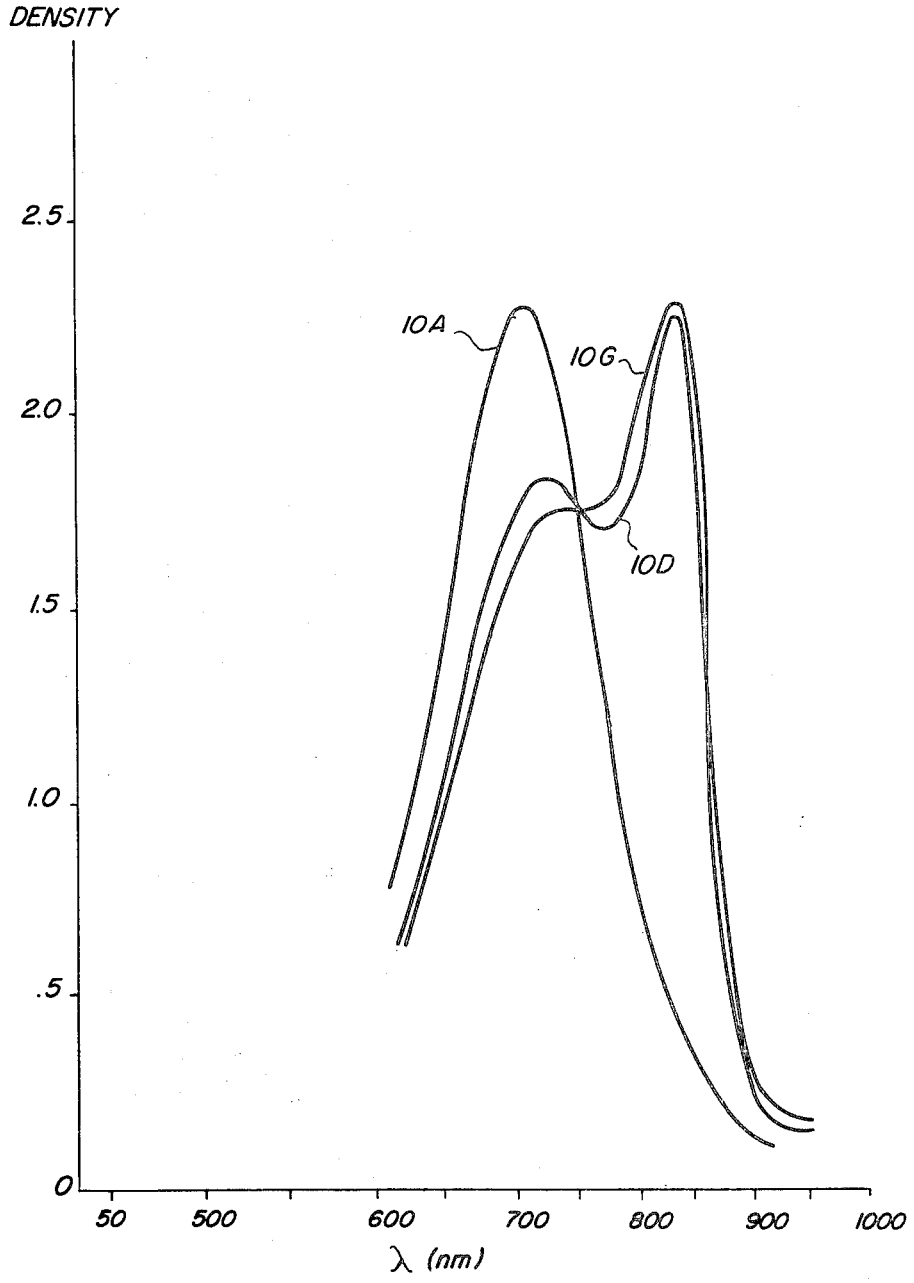
Figure 7:
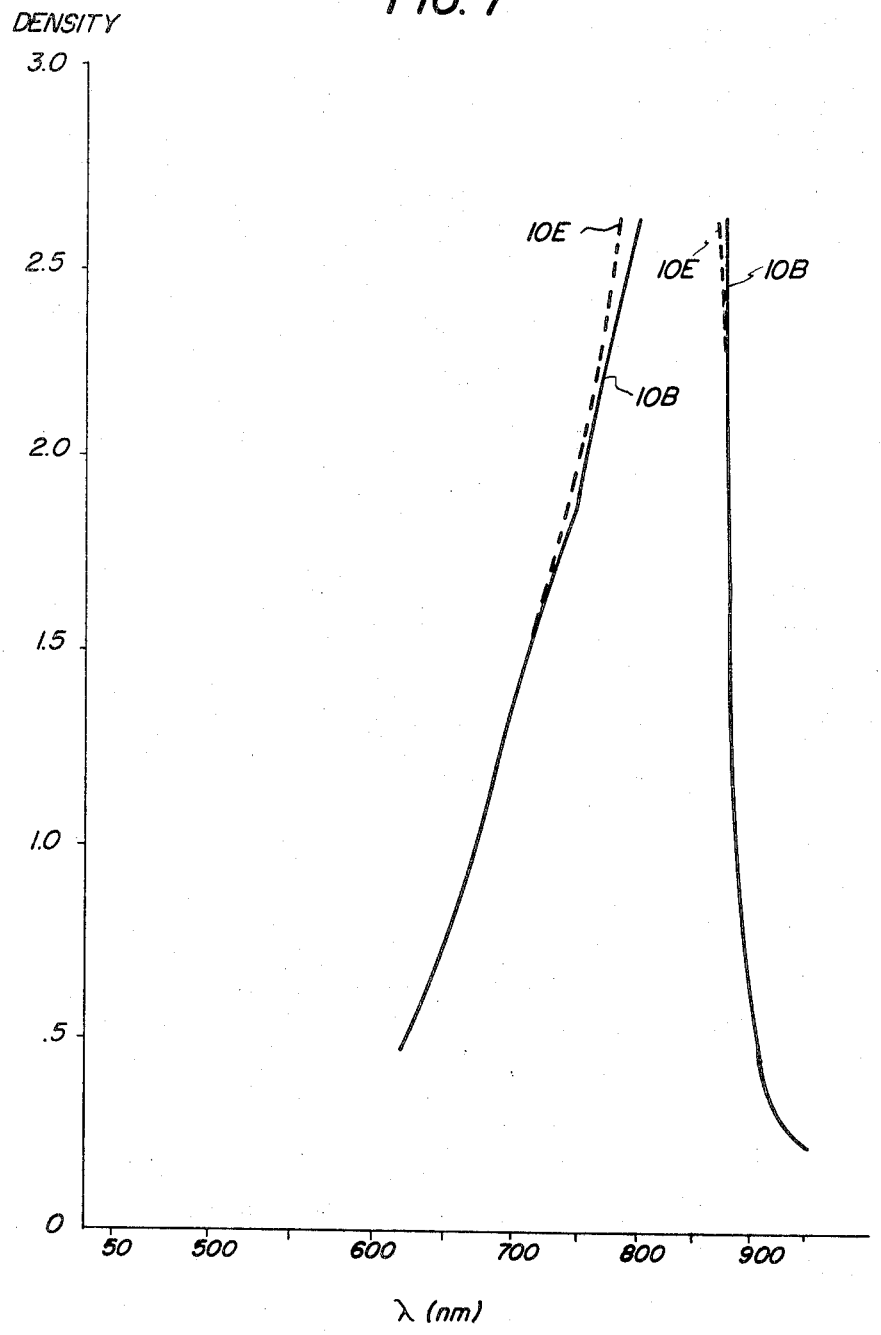
Figure 8:
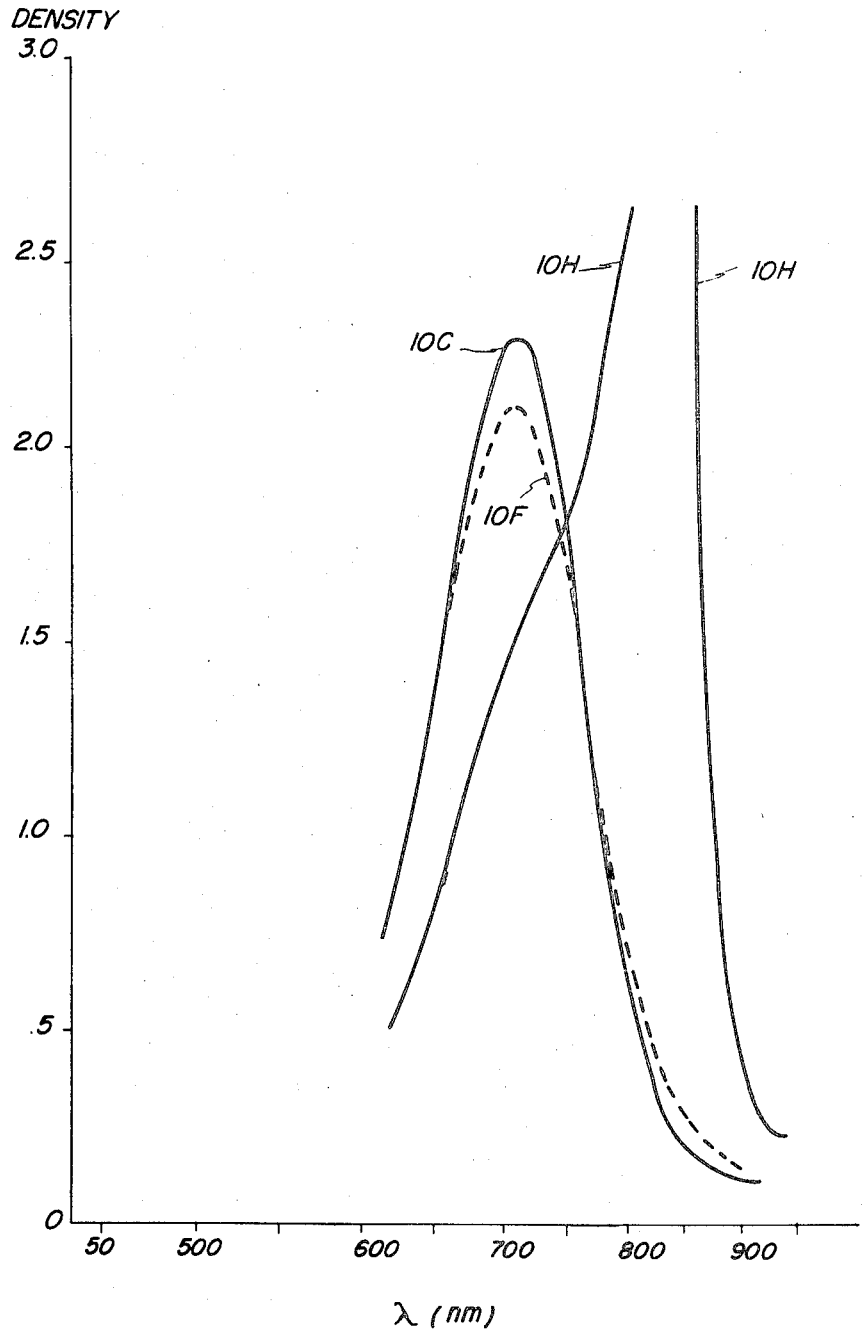
Figure 9:
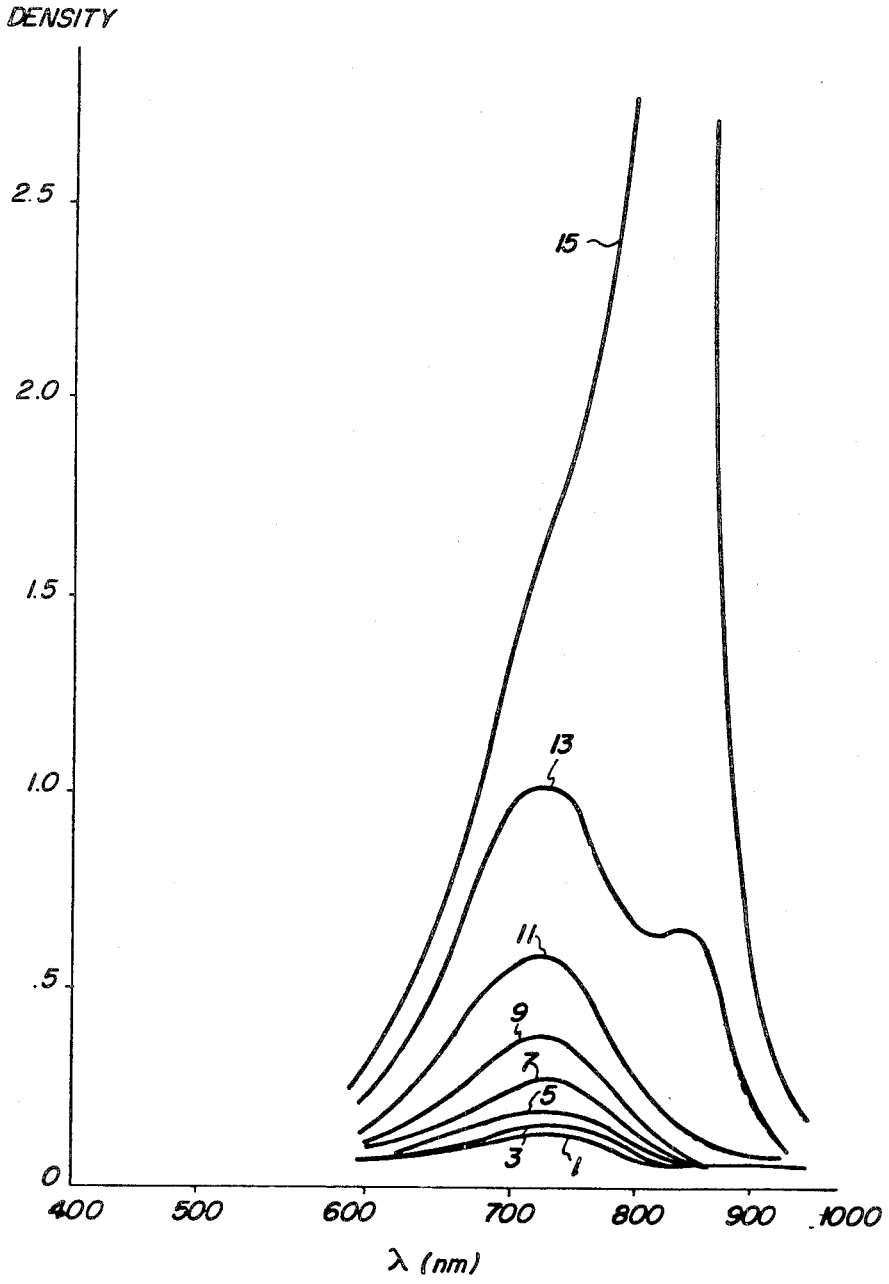
Figure 10:
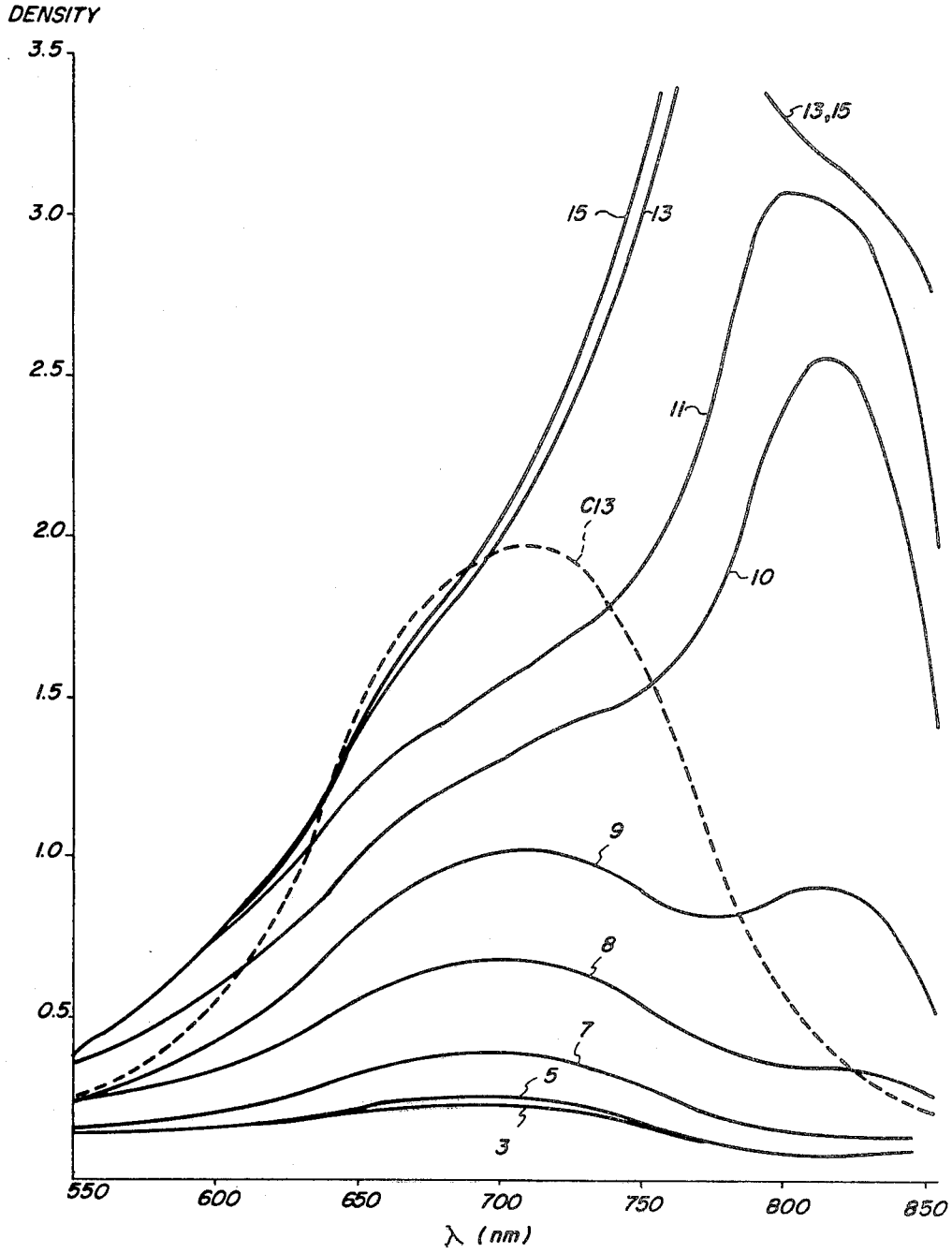
Figure 11:
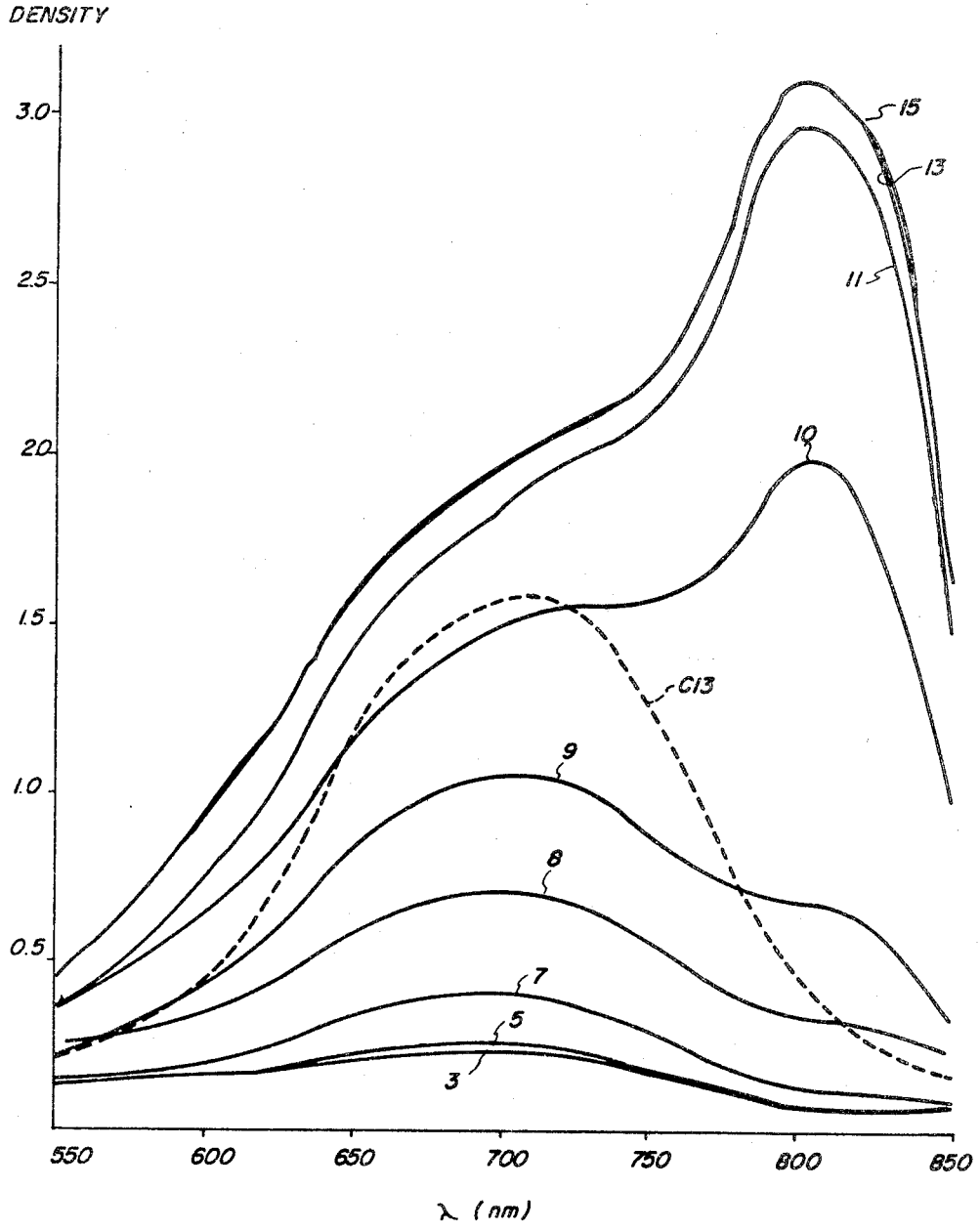

United States Defensive Publication [19] (H) [11] T998,007

Osborn et al. [43] Sep. 2, 1980

[54] PHENYLSULFAMOYL COUPLERS

[76] Inventors: Harland J. Osborn; Robert G. Cameron; Edward J. Walsh, all c/o Kodak Park Division, Rochester, N.Y. 14650

[21] Appl. No.: 103,810

[22] Filed: Dec. 14, 1979

Related U.S. Application Data

[60] Division of Ser. No. 56,587, Jul. 11, 1979, and a continuation-in-part of Ser. No. 928,741, Jul. 27, 1978, abandoned.

[51] Int. Cl.[3] ..... C07C 143/80

[52] U.S. Cl. ..... 260/556 B; 260/556.5

[57] ABSTRACT

Ballasted primary and secondary 3′-sulfamoyl-1-hydroxy-2-naphthanilide couplers are disclosed as well as compositions and photographic elements containing these couplers in coupler solvent particles. The coupler solvent particles are comprised of a combination of a coupler solvent and the coupler capable of permitting the formation of a microcrystalline dye. Surprisingly these microcrystalline dyes exhibit a broadened absorption characteristic in the 750 to 850 mm region of the spectrum. Dye images having such absorption characteristics are particularly suited to forming integral infrared absorbing sound tracks in photographic elements, such as motion picture projection films.

5 Claims, 11 Sheets Drawing,

53 Pages Specification

The file of this unexamined application may be inspected and copies thereof may be purchased (849 O.G. 1221, Apr. 9, 1968).